(12) United States Patent
Yagyu

(10) Patent No.: US 11,694,888 B2
(45) Date of Patent: Jul. 4, 2023

(54) ULTRAVIOLET IRRADIATION DEVICE

(71) Applicant: Ushio Denki Kabushiki Kaisha, Tokyo (JP)

(72) Inventor: Hideaki Yagyu, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 17/785,739

(22) PCT Filed: Dec. 15, 2020

(86) PCT No.: PCT/JP2020/046722
§ 371 (c)(1),
(2) Date: Jun. 15, 2022

(87) PCT Pub. No.: WO2021/149406
PCT Pub. Date: Jul. 29, 2021

(65) Prior Publication Data
US 2023/0054791 A1  Feb. 23, 2023

(30) Foreign Application Priority Data
Jan. 20, 2020 (JP) .................................. 2020-006878

(51) Int. Cl.
H01J 61/02 (2006.01)
H01J 61/16 (2006.01)
(52) U.S. Cl.
CPC ............ H01J 61/025 (2013.01); H01J 61/16 (2013.01)

(58) Field of Classification Search
CPC .................................. H01J 61/025; H01J 61/16
See application file for complete search history.

(56) References Cited

U.S. PATENT DOCUMENTS

2020/0234941 A1* 7/2020 Yagyu ........................ A61L 2/10

FOREIGN PATENT DOCUMENTS

| JP | 2011-048968 A | 3/2011 | |
| JP | 6025756 B2 | 9/2012 | |
| JP | 2018-114197 A | 7/2018 | |
| JP | 2018114197 A * | 7/2018 | ........... A61L 2/0047 |
| WO | 2013/157211 A1 | 10/2013 | |

* cited by examiner

Primary Examiner — Donald L Raleigh
(74) Attorney, Agent, or Firm — Kenichiro Yoshida

(57) ABSTRACT

An ultraviolet irradiation device includes: a lamp house having at least one surface formed with a light extraction surface; an excimer lamp that is accommodated in the lamp house at a position apart from the light extraction surface in a first direction, the excimer lamp emitting ultraviolet light having a main emission wavelength belonging to a first wavelength band of 190 nm or more and 225 nm or less; a pair of electrodes that applies a voltage to a light-emitting tube of the excimer lamp; an optical filter that is disposed on the light extraction surface, and that substantially transmits the ultraviolet light having the first wavelength band and substantially fails to transmit ultraviolet light having a wavelength of 240 nm or more and 300 nm or less; and a light diffuser that is disposed between the excimer lamp and the optical filter in the lamp house in the first direction, for diffusing and reflecting light incident on the light diffuser.

11 Claims, 11 Drawing Sheets

ULTRAVIOLET IRRADIATION DEVICE

TECHNICAL FIELD

The present invention relates to an ultraviolet irradiation device.

BACKGROUND ART

It is conventionally known that DNA exhibits the highest absorption characteristic near a wavelength of 260 nm. A low-pressure mercury lamp shows a high emission spectrum near a wavelength of 254 nm. Hence, conventionally, a technology of sterilizing by the irradiation of ultraviolet light using the low-pressure mercury lamp is widely adopted (refer to, for example, Patent Document 1).

However, light having a wavelength in the vicinity of 254 nm might adversely affect a human body when being irradiated to the human body. The following Patent Document 2 discloses a technology of performing sterilization while avoiding a risk to the human body by using ultraviolet light having a wavelength of 207 nm or more and 220 nm or less in a medical site.

CITATION LIST

Patent Documents

Patent Document 1: JP-A-2011-048968
Patent Document 2: Japanese Patent No. 6025756

SUMMARY OF INVENTION

Technical Problem

However, the above-mentioned Patent Document 2 only refers that the ultraviolet light having a wavelength of 207 nm or more and 220 nm or less may be used for the sterilization in a medical site, and it is not assumed that general consumers and employees of other industries perform general-purpose sterilization treatment in a non-medical site. For example, when ultraviolet light having the above wavelength band is assumed to be used for sterilization of space including living rooms at home, toilets, kitchens, bathrooms, conference rooms, hotel rooms, light sources emitting this ultraviolet light are likely to be installed in places where general consumers and employees of general companies can see them. Hence, such a ultraviolet light source is necessary to be a light source that suitably suppresses adverse effects on the human body.

In view of the above-mentioned problems, an object of the present invention is to provide a ultraviolet irradiation device that suppresses an adverse effect on the human body.

Solution to Problem

An ultraviolet irradiation device according to the present invention includes:

a lamp house having at least one surface formed with a light extraction surface;

an excimer lamp that is accommodated in the lamp house at a position apart from the light extraction surface in a first direction, the excimer lamp emitting ultraviolet light having a main emission wavelength belonging to a first wavelength band of 190 nm or more and 225 nm or less;

an electrode that applies a voltage to a light-emitting tube of the excimer lamp;

an optical filter that is disposed on the light extraction surface, and that substantially transmits the ultraviolet light having the first wavelength band and substantially fails to transmit ultraviolet light having a wavelength of 240 nm or more and 300 nm or less; and a light diffuser that is disposed between the excimer lamp and the optical filter in the lamp house in the first direction, for diffusing and reflecting light incident on the light diffuser.

In the present specification, the "main emission wavelength" refers to a wavelength $\lambda i$ in a wavelength range $Z(\lambda i)$ indicating integrated intensity of 40% or larger with respect to the total integrated intensity in an emission spectrum in a case where a wavelength range $Z(\lambda)$ of $\pm 10$ nm with respect to a certain wavelength $\lambda$, is defined on the emission spectrum. For example, in a light source having an extremely narrow half-value width and exhibiting light intensity only at a specific wavelength such as an excimer lamp in which a luminescent gas containing KrCl, KrBr, and ArF is sealed, a wavelength having the highest relative intensity (main peak wavelength) may be considered as the main emission wavelength.

In the present specification, the description that the optical filter "substantially transmits the ultraviolet light" is intended to mean that the intensity of ultraviolet light transmitted through the optical filter is 60% or larger of the intensity of the ultraviolet light incident on the optical filter. In the present specification, the description "substantially fail to transmit the ultraviolet light" is intended to mean that the intensity of ultraviolet light transmitted through the optical filter is less than 20% of the intensity of the ultraviolet light incident on the optical filter.

Note that the optical filter may substantially reflect the ultraviolet light having a wavelength of 240 nm or more and 300 nm or less. Here, in the present specification, the description "substantially reflect the ultraviolet light" is intended to mean that the intensity of ultraviolet light reflected by the optical filter is 80% or larger of the intensity of the ultraviolet light incident on the optical filter.

Transmittance and reflectance of the ultraviolet light on the optical filter actually change depending on an incident angle of the ultraviolet light incident on the optical filter. Here, the ultraviolet light emitted from the excimer lamp travels with a certain divergence angle; among all the traveling light, intensity of the light traveling at an angle in the vicinity of 0° with respect to the normal of a light emission surface is the strongest, and the intensity decreases as the divergence angle is farther from 0°. Hence, the optical filter having a transmittance of 60% or larger with respect to the intensity of the ultraviolet light incident on the optical filter at an incident angle of 20° or smaller may be treated as a filter that substantially transmits the ultraviolet light. Similarly, the optical filter having a transmittance of less than 20% with respect to the intensity of the ultraviolet light incident on the optical filter at an incident angle of 20° or smaller may be treated as a filter that substantially fails to transmit the ultraviolet light. Similarly, the optical filter having a reflectance of 90% or larger with respect to the intensity of the ultraviolet light incident on the optical filter at an incident angle of 20° or smaller may be treated as a filter that substantially reflects the ultraviolet light.

The excimer lamps that emit the ultraviolet light having its main emission wavelength belonging to the first wavelength band, may also emit ultraviolet light having a wavelength band (wavelength of 240 nm or more and 300 nm or less) that may adversely affect the human body although intensity thereof is extremely small. FIG. 1 is a graph illustrating an example of an emission spectrum of an excimer lamp (main peak wavelength is in the vicinity of 222 nm) containing KrCl as a luminescent gas.

With reference to FIG. 1, the output of light having a wavelength band of 240 nm or longer is observed also although it is faint. Note that in addition to the excimer lamp containing KrCl as a luminescent gas, other excimer lamps that emit the ultraviolet light having its main emission wavelength belonging to the first wavelength band, such as an excimer lamp containing KrBr as a luminescent gas (main peak wavelength is 207 nm) and an excimer lamp containing ArF as a luminescent gas (main peak wavelength is 193 nm), may similarly emit the ultraviolet light having a wavelength of 240 nm or more and 300 nm or less.

As described above, in the ultraviolet irradiation device according to the present invention, the optical filter that substantially transmits the ultraviolet light having the first wavelength band and substantially reflects the ultraviolet light having a wavelength of 240 nm or more and 300 nm or less is disposed on the side of the light extraction surface. Hence, components of light having a wavelength of 240 nm or more and 300 nm or less contained in the ultraviolet light emitted from the excimer lamp are substantially reflected by the optical filter, thus the amount of the components of light extracted out of the ultraviolet irradiation device decreases. Therefore, providing such optical filter reduces the amount of the components of light extracted to the outside even though the components are originally those of light having a wavelength band with a small output, further suppressing the adverse effect on the human body.

Incidentally, as described above, transmittance and reflectance of the ultraviolet light on the optical filter change depending on the incident angle of the ultraviolet light incident on the optical filter. Even in the ultraviolet light having the first wavelength band, which is intended to be extracted from the ultraviolet irradiation device, the transmittance decreases and the reflectance increases when the incident angle on the optical filter becomes extremely large. In this case, among the ultraviolet light having the first wavelength band emitted from the excimer lamp, a part of the ultraviolet light incident on the optical filter at a relatively large incident angle (for example, 30° or larger) is reflected by the optical filter and returned toward the excimer lamp. As a result, this light is not extracted out of the ultraviolet irradiation device, lowering the light extraction efficiency to a certain extent as compared with a case in which no optical filter is provided.

In contrast, the ultraviolet irradiation device according to the present invention is provided with a light diffuser that is disposed closer to the excimer lamp than the optical filter in the lamp house with respect to the first direction, and diffuses light incident on the light diffuser. Hence, even if ultraviolet light having the first wavelength band emitted from the excimer lamp and incident on the optical filter at a relatively large incident angle is reflected by the optical filter, at least a part of the ultraviolet light is incident on the light diffuser, and is diffused and reflected by the light diffuser. Since at least a part of the diffused light is incident on the optical filter at a relatively small angle of incidence, it passes through the optical filter as it is and is extracted from the light extraction surface to the outside of the lamp house.

In other words, this configuration allows a proportion of the ultraviolet light transmitted through the optical filter to increase, compared with the case in which no light diffuser is provided, thus increasing the output of the ultraviolet light having the first wavelength band extracted from the ultraviolet irradiation device.

Note that, the description "the optical filter is disposed on the light extraction surface" includes a case in which the optical filter is disposed in a position apart from the light extraction surface at a minute distance (for example, a few millimeters to dozen millimeters) in the first direction as well as a case in which the optical filter is disposed so as to be completely integrated with the light extraction surface.

The light diffuser can be disposed at various locations.

The pair of electrodes may include, for example, a pair of electrode blocks that is disposed apart in an axial direction of the light-emitting tube of the excimer lamp such that a portion of each of the electrode blocks is in contact with a tube wall of the light-emitting tube thereof, and the light diffuser may be formed on a surface of an area of at least one of the electrode blocks, the surface facing the optical filter.

In this case, the light diffuser may include an uneven area formed on the surface of the electrode block.

For another example, the light diffuser may include a first light diffusion plate that is disposed in the lamp house, on the opposite side of the light extraction surface in the first direction, and between the pair of electrodes.

The first light diffusion plate can include a sheet material or a coated film consisting of fine particles of inorganic materials such as alumina and silica or fine particles of fluorinated resin materials such as polytetrafluoroethylene (PTFE).

For another example, the light diffuser may include a second light diffusion plate that is disposed in the lamp house in a manner to sandwich or surround the optical filter when viewed in the first direction.

This second light diffusion plate, similar to the first light diffusion plate described above, can also include a sheet material or a coated film consisting of fine particles of inorganic materials such as alumina and silica, or fine particles of fluorinated resin materials such as polytetrafluoroethylene (PTFE).

Advantageous Effects of Invention

According to the present invention, achieved is an ultraviolet irradiation device that suppresses the degree of adverse effects on the human body while suppressing a decrease in the light extraction efficiency of the first ultraviolet light.

DESCRIPTION OF EMBODIMENTS

Figure 1:
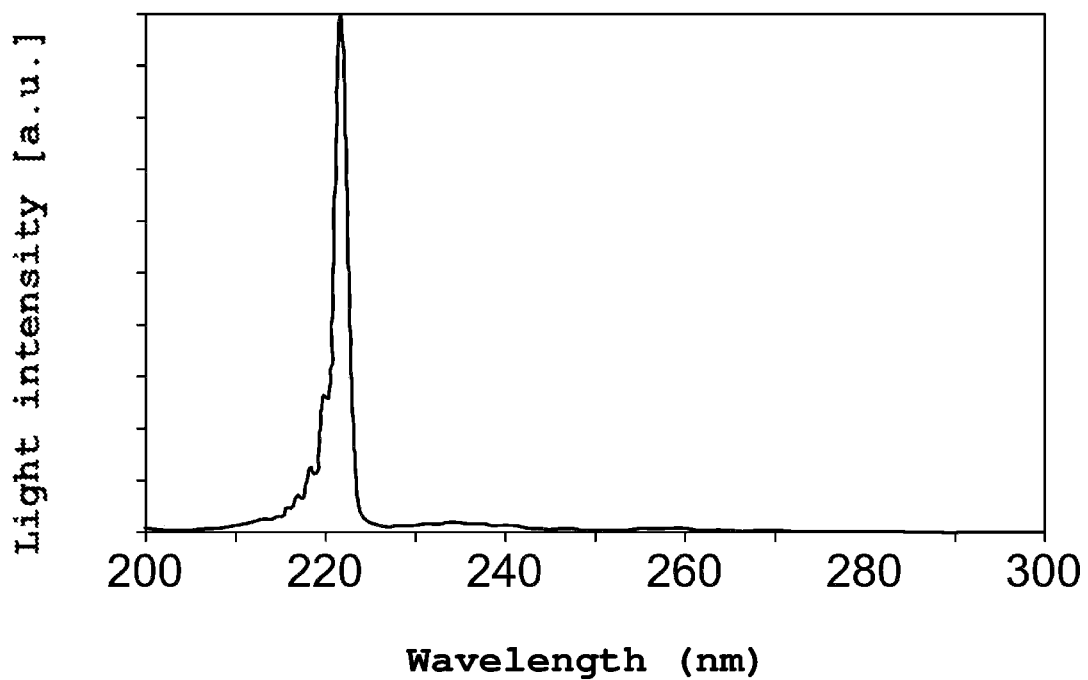
FIG. 1 is an example of an emission spectrum of an excimer lamp in which a luminescent gas contains KrCl.

Embodiments of an ultraviolet irradiation device according to the present invention will be described with reference to the drawings as appropriate. Note that the following drawings are schematically illustrated, and a dimensional ratio on the drawing and an actual dimensional ratio do not always match. Furthermore, the dimensional ratios do not always the same between the drawings.

First Embodiment

Hereinafter, a first embodiment of an ultraviolet irradiation device will be described.

Figure 2:
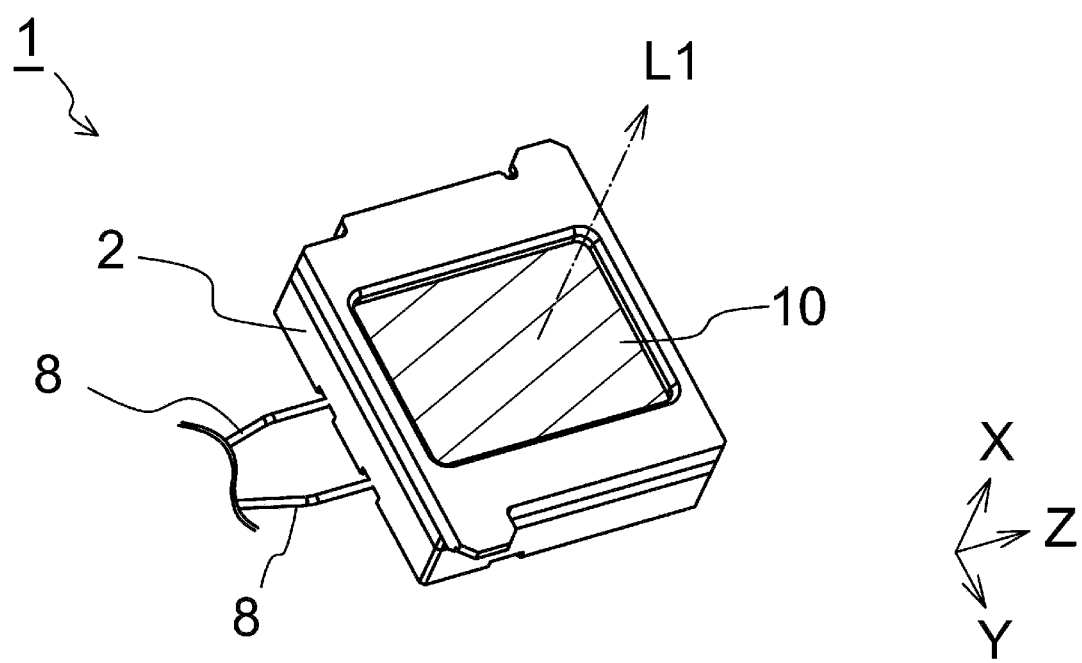
FIG. 2 is a perspective view schematically illustrating an appearance of an ultraviolet irradiation device according to a first embodiment.
Figure 3:
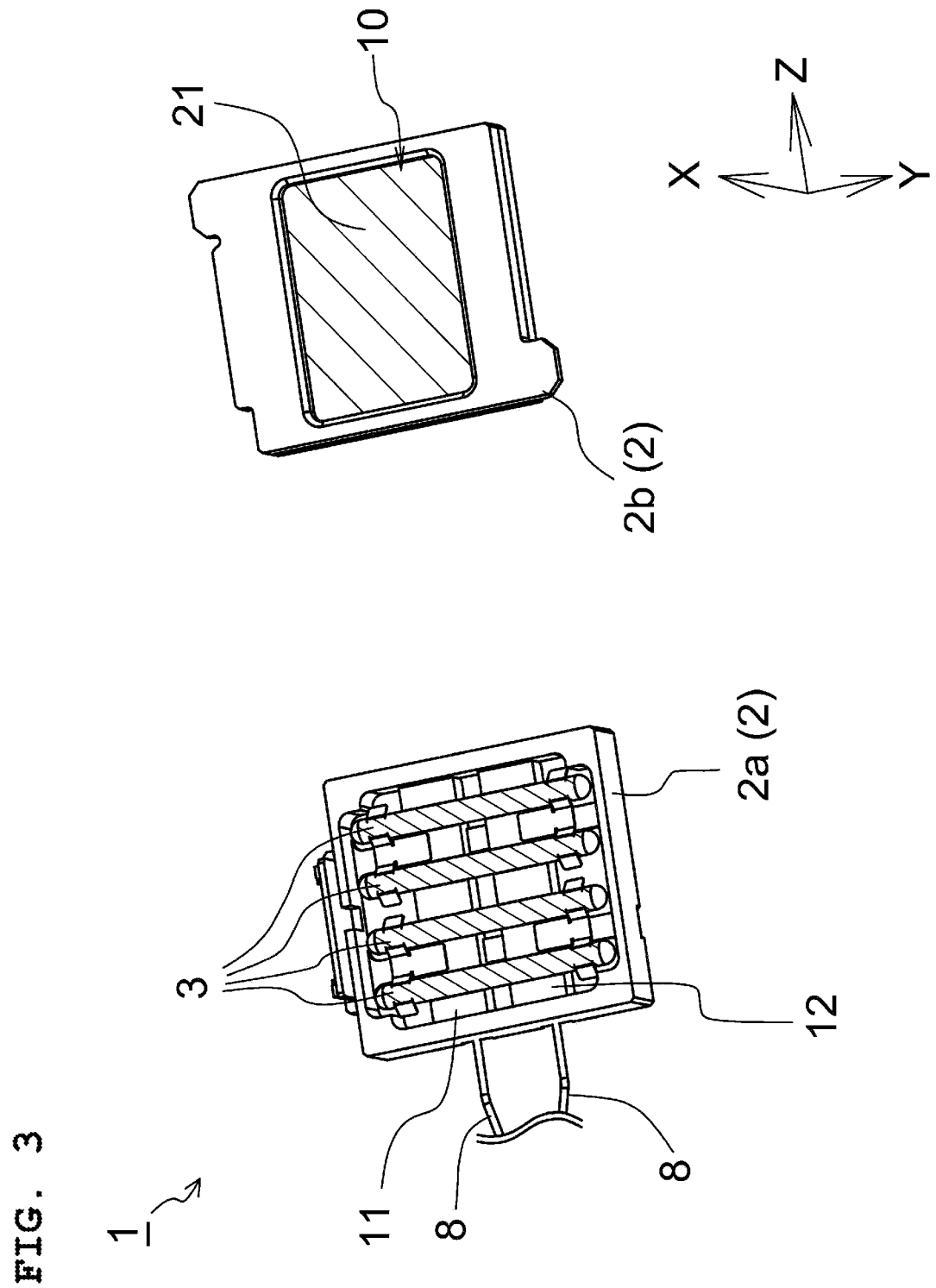
FIG. 3 is an exploded perspective view of a main body casing and a lid of a lamp house of the ultraviolet irradiation device in FIG. 2.

FIG. 2 is a perspective view schematically illustrating an appearance of the first embodiment of the ultraviolet irradiation device. FIG. 3 is an exploded perspective view of a main body casing 2a and a lid 2b of a lamp house 2 of the ultraviolet irradiation device 1 in FIG. 2.

Each of the following drawings is illustrated with reference to an X-Y-Z coordinate system in which an extraction direction of ultraviolet light L1 is defined as an X direction, and a plane orthogonal to the X direction is defined as a YZ plane. In further detail, as described later with reference to FIG. 3 and subsequent drawings, a tube axis direction of an excimer lamp 3 is defined as a Y direction, and a direction orthogonal to the X direction and the Y direction is defined as a Z direction. The X direction corresponds to a "first direction".

As illustrated in FIGS. 2 and 3, the ultraviolet irradiation device 1 is provided with the lamp house 2 having one surface formed with a light extraction surface 10. The lamp house 2 is provided with the main body casing 2a and the lid 2b, and the excimer lamp 3 and electrode blocks (11, 12) are accommodated in the main body casing 2a.

As illustrated in FIGS. 2 and 3, an optical filter 21 is provided in an area that forms the light extraction surface 10 of the lid 2b, which constitutes the part of the lamp house 2. A characteristic of the optical filter 21 will be described later.

Although a case in which four excimer lamps 3 (3a, 3b, 3c, 3d) are accommodated in the lamp house 2 is described as an example in the present embodiment (refer to FIG. 4), note that the number of the excimer lamps 3 may be one, two, three, or five or more. The electrode blocks (11, 12) are electrically connected to power feed lines 8, and form electrodes for supplying power to each excimer lamp 3.

Figure 4:
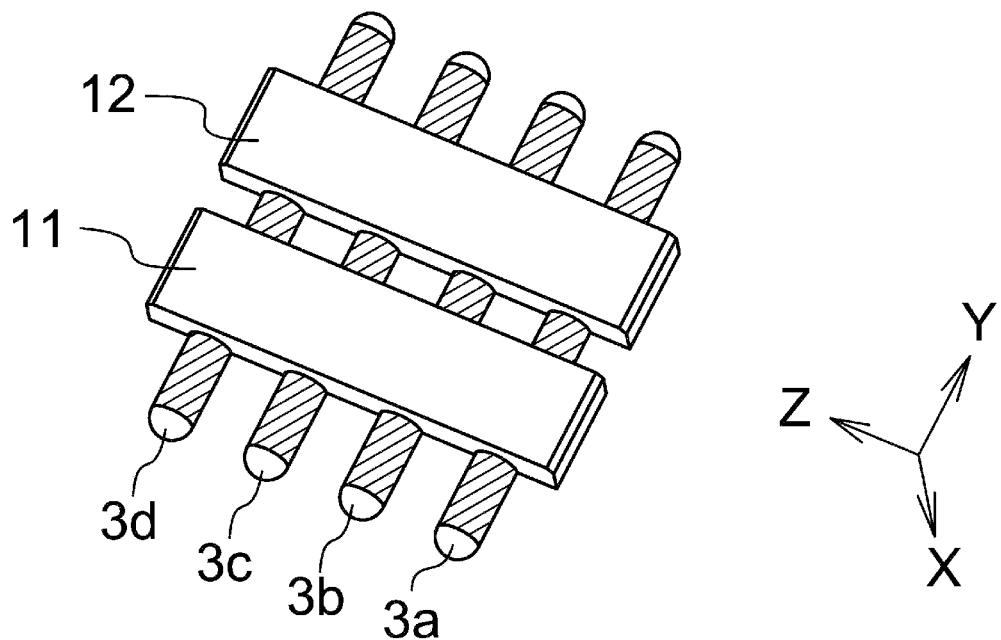
FIG. 4 is a perspective view schematically illustrating a structure of electrode blocks and an excimer lamp provided in the ultraviolet irradiation device.
Figure 5:
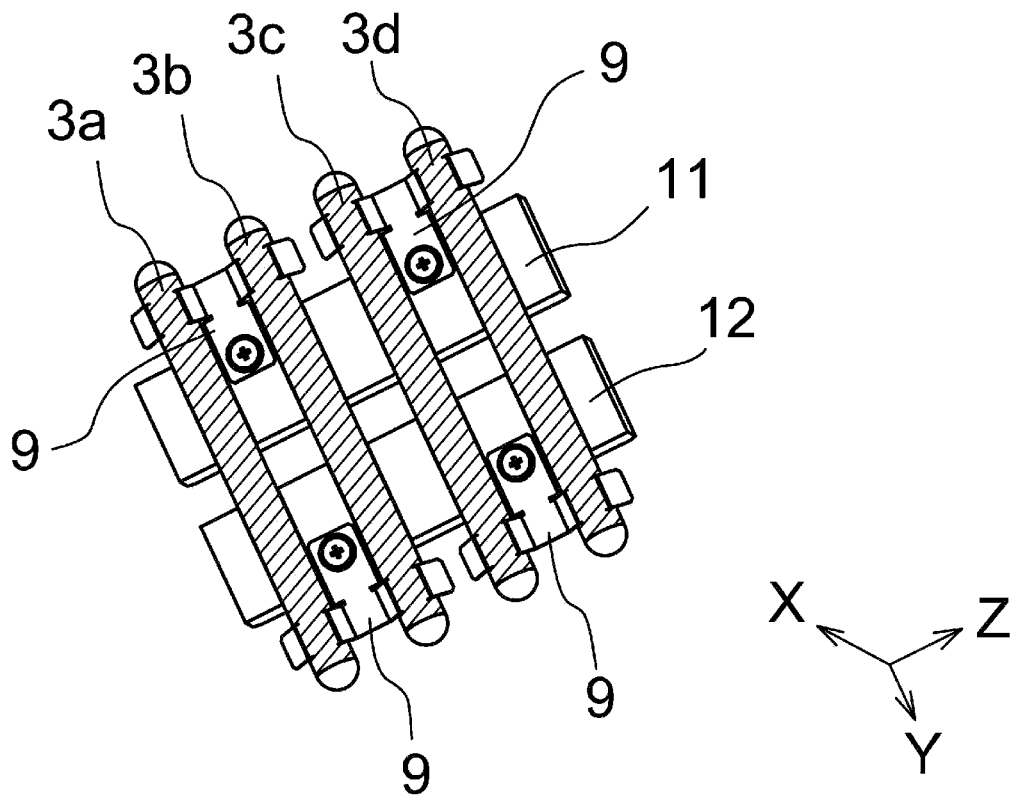
FIG. 5 is a perspective view with a viewing point different from that of FIG. 4.

FIGS. 4 and 5 are perspective views omitting to illustrate the main body casing 2a, which constitutes the part of the lamp house 2, from FIG. 3, extracting only the electrode blocks (11, 12) and the excimer lamps 3 (3a, 3b, 3c, 3d) and illustrating them. FIGS. 4 and 5 are views with different viewing points each other. In FIG. 5, a holder 9 for holding the electrode blocks (11, 12) and the excimer lamp 3 is also illustrated. In FIG. 4, the holder 9 is omitted for convenience of illustration.

Figure 6:
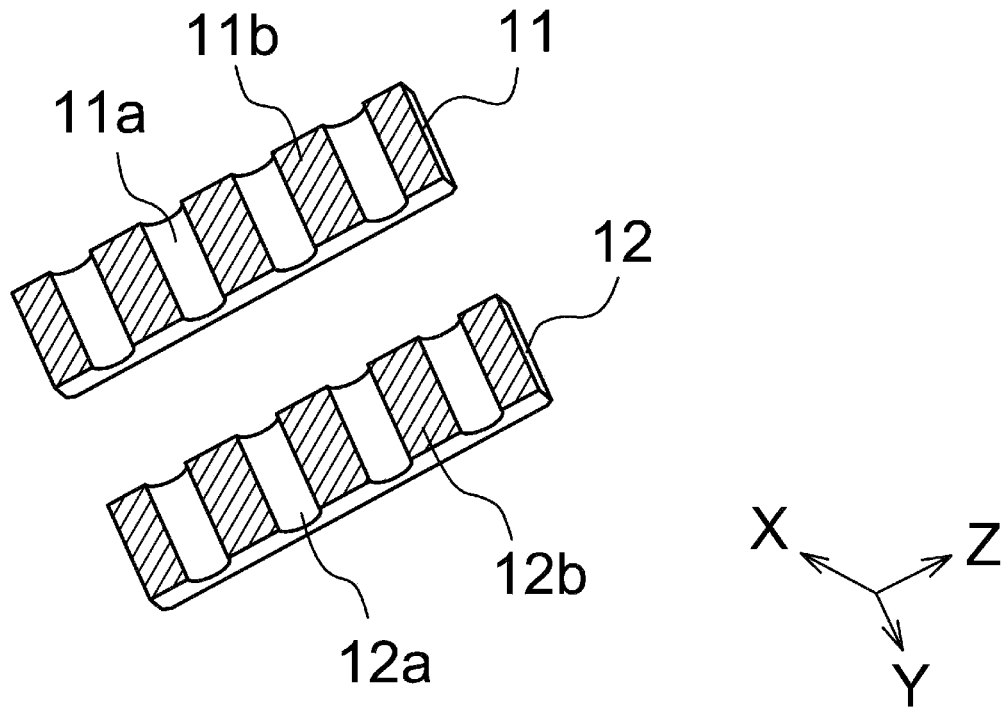
FIG. 6 is a perspective view schematically illustrating the structure of the electrode blocks.

FIG. 6 is a perspective view extracting only the electrode blocks (11, 12) from FIG. 5 and illustrating them.

As illustrated in FIGS. 3 to 5, the ultraviolet irradiation device 1 of the present embodiment is provided with the four excimer lamps 3 (3a, 3b, 3c, 3d) arranged so as to be apart from each other in the Z direction. The two electrode blocks (11, 12) are arranged so as to be in contact with an outer surface of a light-emitting tube of each excimer lamp 3.

The electrode blocks (11, 12) are arranged in positions apart from each other in the Y direction. In the example illustrated in FIG. 6, the electrode block 11 includes mounting areas 11a each having a shape along a curved surface of the outer surface of the light-emitting tube of the excimer lamp 3 on which the excimer lamps 3 are to be mounted. The electrode block 12 also includes mounting areas 12a on which the excimer lamps 3 are to be mounted.

In the present embodiment, light diffusion surfaces 11b are formed in the areas other than the mounting areas 11a among the area of the electrode block 11 facing the light extraction surface 10. Similarly, light diffusion surfaces 12b are formed in the areas other than the mounting areas 12a among the area of the electrode block 12 facing the light extraction surface 10.

The light diffusion surface 11b and the light diffusion surface 12b are formed to diffuse and reflect the ultraviolet light L1 emitted from the excimer lamp 3 when the ultraviolet light L1 is incident thereon. The light diffusion surfaces (11b, 12b), for example, may be areas on which unevenness is has been formed, the areas being surfaces of the metal material constituting the electrode block (11, 12). The light diffusion surfaces (11b, 12b), for another example, may be areas each on which a sheet material or a coated film consisting of fine particles of inorganic materials such as alumina or silica or fine particles of fluorinated resin such as polytetrafluoroethylene (PTFE) is formed, the areas being surfaces of the electrode block (11, 12).

The function of this light diffusion surface (11b, 12b) will be described later along with the characteristics of the optical filter 21.

In the example shown in FIG. 6, the electrode block 11 is illustrated such that the light diffusion surfaces 11b are formed in all the areas of the electrode block 11 that face the light extraction surface 10, other than the mounting areas 11a; however, the light diffusion surfaces 11b are formed in at least a part of the areas other than the mounting areas 11a. The same is true for the light diffusion surface 12b.

The electrode blocks (11, 12) are made of conductive materials, preferably materials that exhibit reflectivity to the ultraviolet light emitted from the excimer lamp 3. Both of the electrode blocks (11, 12) are made of, for example, Al, Al alloys, and stainless steel.

Both of the electrode blocks (11, 12) are arranged to be in contact with the outer surface of the light-emitting tube of each of the excimer lamps 3 (3a, 3b, 3c, 3d) and straddle the respective excimer lamps 3 with respect to the Z direction.

Figure 7:
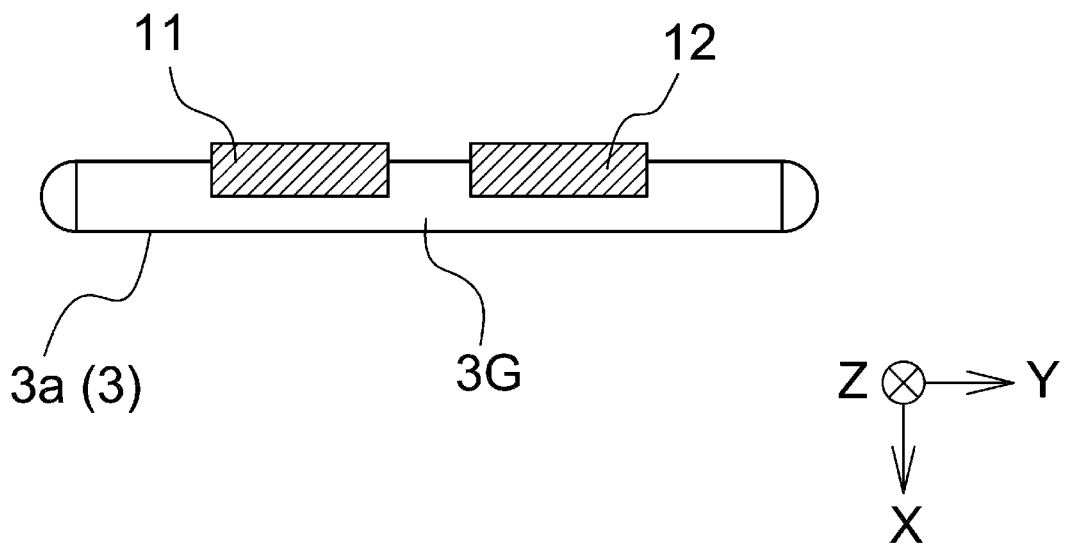
FIG. 7 is a schematic plan view of the perspective view in FIG. 4 as seen in the +Z direction.

FIG. 7 is a drawing schematically illustrating a positional relationship between the excimer lamp 3 and the electrode blocks (11, 12), the drawing corresponding to the schematic plan view of the excimer lamp 3 when seen in the Z direction. Among the four excimer lamps 3 (3a, 3b, 3c, 3d), only the excimer lamp 3a, which is located at the farthest in the −Z direction, is shown in FIG. 7. The other excimer lamps (3b, 3c, 3d) are omitted to be illustrated from the figure; however, as mentioned above, the excimer lamps (3b, 3c, 3d) are also arranged in the +Z direction.

The excimer lamp 3 includes the light-emitting tube having its tube axis direction in the Y direction, and the outer surface of the light-emitting tube of the excimer lamp 3 is in contact with each of the electrode blocks (11, 12) at positions apart from each other in the Y direction. A luminescent gas 3G is sealed in the light-emitting tube of the excimer lamp 3. Applying a high-frequency AC voltage of, for example, about 10 kHz to 5 MHz between the electrode blocks (11, 12) through the power feed lines 8 (shown in FIG. 2) causes the voltage to be applied to the luminescent gas 3G via the light-emitting tube of the excimer lamp 3. Then, discharge plasma is generated in a discharge space in which the luminescent gas 3G is sealed, exciting an atom of the luminescent gas 3G to an excimer state, and generating excimer light emission when this atom relaxes to a ground state.

The luminescent gas 3G includes a material that emits the ultraviolet light L1 having a main emission wavelength belonging to a first wavelength band of 190 nm or more and 225 nm or less at the time of excimer light emission. Example of the luminescent gas 3G includes KrCl, KrBr, and ArF. Note that, in addition to the above-described gas types, an inert gas such as argon (Ar) or neon (Ne) may also be mixed.

For example, the luminescent gas 3G containing KrCl allows the excimer lamp 3 to emit the ultraviolet light L1 having a main peak wavelength in the vicinity of 222 nm. The luminescent gas 3G containing KrBr allows the excimer lamp 3 to emit the ultraviolet light L1 having a main peak wavelength in the vicinity of 207 nm. The luminescent gas 3G containing ArF allows the excimer lamp 3 to emit the ultraviolet light L1 having a main peak wavelength in the vicinity of 193 nm. The spectrum of the ultraviolet light L1 emitted from the excimer lamp 3 in which the luminescent gas 3G contains KrCl is described above with reference to FIG. 1.

As illustrated in FIG. 1, the spectrum of the ultraviolet light L1 has a profile in which its light output is concentrated in the vicinity of 222 nm, which is substantially the main peak wavelength; however its light output in the wavelength band of 240 nm or longer, which might adversely affect a human body, is also slightly observed when the luminescent gas 3G contains KrCl. Hence, the optical filter 21 is provided in the area constituting the light extraction surface 10 to block light components in this wavelength band.

Figure 8:
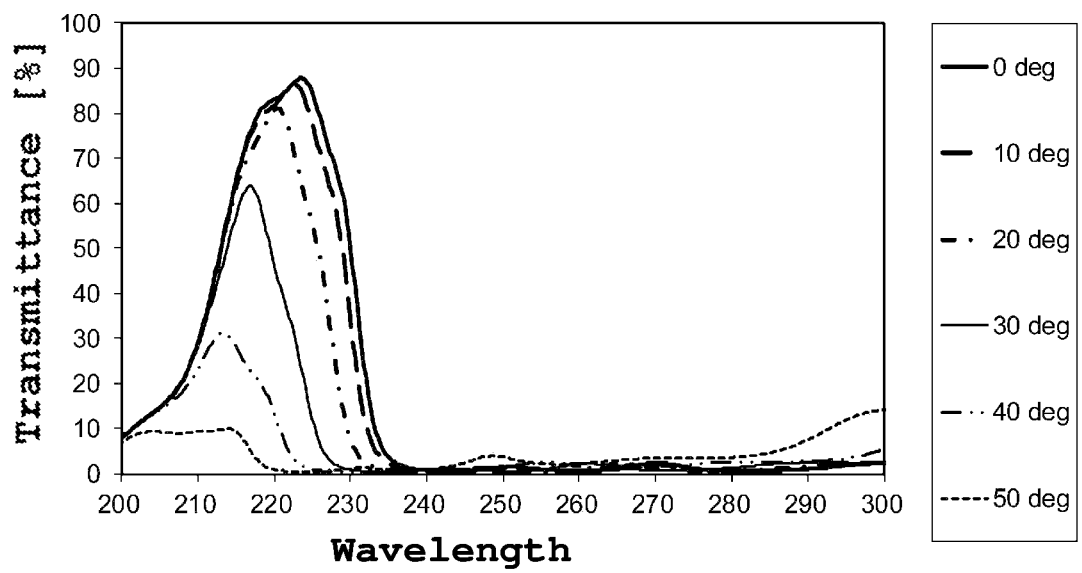
FIG. 8 is a graph illustrating an example of a transmission spectrum of an optical filter.
Figure 9:
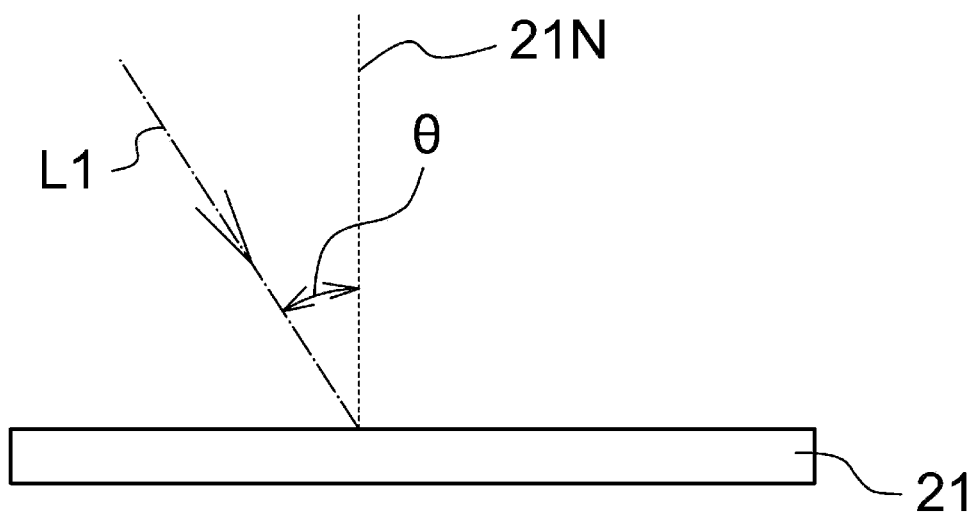
FIG. 9 is a schematic diagram for explaining an incident angle of ultraviolet light on the optical filter.

FIG. 8 is a graph illustrating an example of a transmission spectrum of the optical filter 21, the transmission spectrum being measured as a ratio of intensity of light emitted through the optical filter 21 to intensity of light incident on the optical filter 21 per wavelength. Note that, in FIG. 8, the transmission spectrum is illustrated with respective incident angles θ at which the ultraviolet light L1 is incident on the optical filter 21. Here, the incident angle θ is defined as an angle between a normal line 21N with respect to an incident surface of the optical filter 21 and the ultraviolet light L1 incident on the incident surface of the optical filter 21 as illustrated in FIG. 9.

The optical filter 21 having a characteristic illustrated in FIG. 8 is designed to be used in a case in which the luminescent gas 3G of the excimer lamp 3 contains KrCl, in other words, a case in which the excimer lamp 3 emits the ultraviolet light L1 having a main peak wavelength of 222 nm. Hence, as illustrated in FIG. 8, this optical filter 21 substantially transmits the ultraviolet light L1 having a wavelength in the vicinity of 222 nm, more specifically a wavelength band of 218 nm or more and 226 nm or less, but substantially fails to transmit the ultraviolet light L1 of 240 nm or more and 300 nm or less. The optical filter 21 may be designed to substantially transmit the ultraviolet light L1 having wavelength components in the vicinity of the main peak wavelength and also substantially fail to transmit the ultraviolet light L1 of 240 nm or more and 300 nm or less among the ultraviolet light L1 emitted from the excimer lamp 3.

In the ultraviolet light L1 of 240 nm or more and 300 nm or less, the optical filter 21 described in FIG. 8 exhibits transmittance of 5% or less with an incident angle θ in a range from 0° to 40°, and exhibits transmittance of 10% or less even with an incident angle θ of 50°.

As described above, the optical filter 21 exhibiting different transmittance depending on the wavelength of the ultraviolet light L1 incident thereon is achieved by a dielectric multilayer film composed of a plurality of materials having different refractive indices. However, when the optical filter 21 is formed of the dielectric multilayer film composed of the plurality of materials having different refractive indices, the transmittance unavoidably varies depending on the incident angle θ of the ultraviolet light L1 with respect to the optical filter 21. As a result, as illustrated in FIG. 8, the transmittance in the vicinity of the main peak wavelength (222 nm, in this example) also decreases depending on the incident angle θ of the ultraviolet light L1 with respect to the optical filter 21. With reference to FIG. 8, when the incident angle θ is, for example, 40° or larger, the transmittance with respect to the ultraviolet light L1 in the vicinity of 222 nm is less than 20%.

Figure 10:
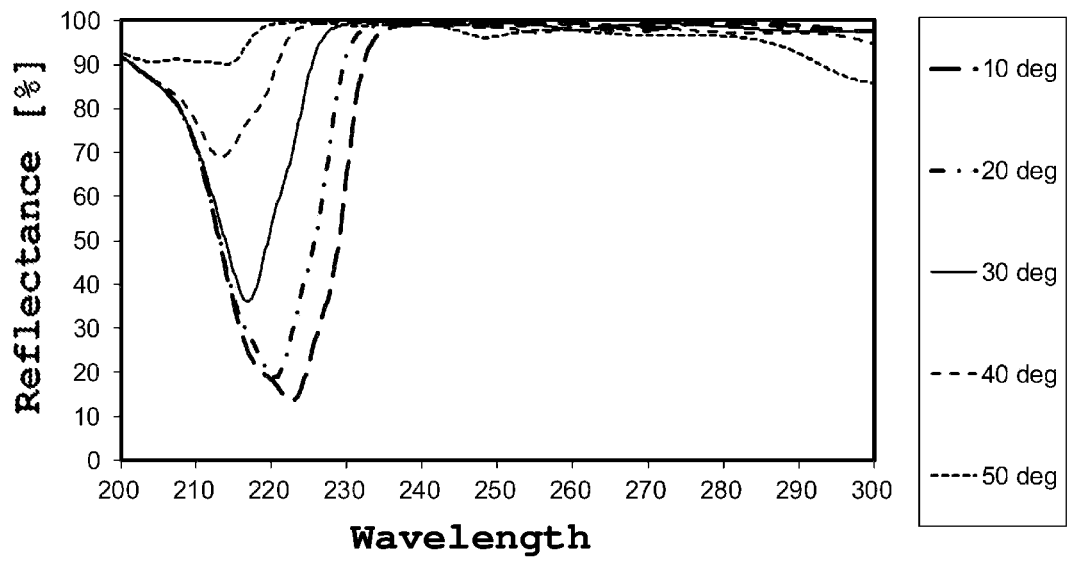
FIG. 10 is a graph illustrating an example of a reflection spectrum of the optical filter.

Note that, among the ultraviolet light L1, a part of the ultraviolet light L1, which fails to be transmitted through the optical filter 21, is reflected by the optical filter 21. FIG. 10 is a graph illustrating an example of a reflection spectrum of the optical filter 21, the reflection spectrum being measured as a ratio of intensity of light reflected by the optical filter 21 to intensity of light incident on the optical filter 21 per wavelength. However, since a light emission unit and a light reception unit cannot be arranged on the same optical axis, data at an incident angle θ of 0° is not illustrated in the graph in FIG. 10.

In the ultraviolet light L1 of 240 nm or more and 300 nm or less, the optical filter 21 described in FIG. 10 exhibits reflectance of 95% or more with an incident angle θ in a range from 10° to 40°, and exhibits reflectance of 90% or more even with an incident angle θ of 50°.

Figure 11:
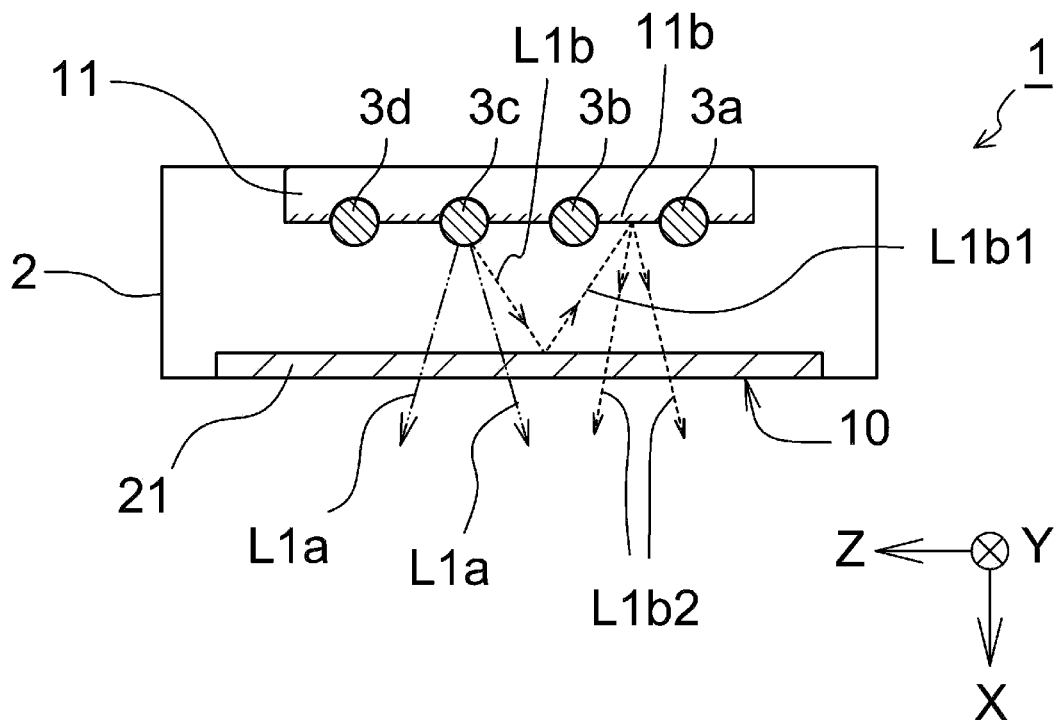
FIG. 11 is a cross-sectional view schematically illustrating the ultraviolet irradiation device of the first embodiment cut in a plain parallel to the XZ plain.

Next, the effects of the light diffusion surfaces (11b, 12b) provided on the surfaces of the electrode blocks (11, 12) are described with reference to the drawings. FIG. 11 is a schematic cross-sectional view of the ultraviolet irradiation device 1 of the present embodiment when cut in a plane parallel to the XZ plane at a predetermined position in the Y coordinate. FIG. 11 schematically illustrates the travelling state of the ultraviolet light L1 emitted from the excimer lamp 3 and directed toward the optical filter 21. In FIG. 11, the ultraviolet light L1 emitted from the excimer lamp 3c is typically illustrated as an example among the ultraviolet light L1 emitted from each of the excimer lamps 3. Note that the signs L1a, L1b, L1b1, and L1b2 in FIG. 11 each indicate a part of ultraviolet light L1.

The ultraviolet light L1 emitted from each excimer lamp 3 travels toward the optical filter 21 with a predetermined divergence angle. Hence, among the ultraviolet light L1, the ultraviolet light L1a, which has a relatively small incident angle with respect to the optical filter 21, is substantially transmitted through the optical filter 21, including components in the vicinity of the main peak wavelength. In contrast, the ultraviolet light L1b, which has a relatively large incident angle with respect to the optical filter 21, is reflected by the optical filter 21 at a certain proportion, including even the components in the vicinity of the main peak wavelength. This reflected light travels toward the opposite direction (−X direction) to the light extraction direction.

(Ultraviolet Light L1b1)

Here, the ultraviolet irradiation device 1 of the present embodiment has the light diffusion surface 11b formed on the surface of the electrode block 11. Hence, a part of the ultraviolet light L1b1 is incident on this light diffusion surface 11b, diffused and reflected (ultraviolet light L1b2). A part of the diffused and reflected ultraviolet light L1b2 is incident on the optical filter 21 at an incident angle smaller than that of ultraviolet light L1b. As a result, a part of the ultraviolet light L1b2 is transmitted through the optical filter 21 and is extracted outside of the ultraviolet irradiation device 1. This configuration improves light extraction efficiency compared to the case in which no light diffusion surface 11b is provided. The same is true for the light diffusion surface 12b on the side of the electrode block 12.

EXAMPLE OF EMBODIMENT

Example 1 is defined as the ultraviolet irradiation device 1 including the electrode block 11 provided with a PTFE sheet on the surface thereof facing the light extraction surface 10 to form the light diffusion surface 11b, and the electrode block 12 similarly provided with a PTFE sheet on the surface thereof facing the light extraction surface 10 to form the light diffusion surface 12b. Reference Example 1 is defined as an ultraviolet irradiation device in which a PTFE sheet was not provided on the surface of each of the electrode blocks (11, 12). With the ultraviolet irradiation devices of Example 1 and Reference Example 1 being turned on, the illuminance on the irradiation surface located outside the light extraction surface 10 was measured with an illuminance meter. Table 1 below shows the illuminance on the irradiation surface outside the light extraction surface 10.

TABLE 1

| | | Illuminance (relative value) |
|---|---|---|
| Reference Example 1 | Without PTFE | 1.00 |
| Example 1 | With PTFE | 1.17 |

Example 2 is defined as the ultraviolet irradiation device 1 including the electrode block 11 having a surface facing the light extraction surface 10, the surface being an uneven area by being roughened with a #500 grit abrasive to form the light diffusion surface 11b, and the electrode block 12 having a surface facing the light extraction surface 10, the surface similarly being an uneven area by being roughened to form the light diffusion surface 12b. Reference Example 1, as similar to the above, is defined as an ultraviolet irradiation device in which the light diffusion surfaces (11b, 12b) were not formed on the surface of the electrode blocks (11, 12), respectively. In detail, the electrode blocks (11, 12) each have a mirror surface. With the ultraviolet irradiation devices of Example 2 and Reference Example 1 being turned on, the illuminance on the irradiation surface located outside the light extraction surface 10 was measured. Table 2 below shows the illuminance on the irradiation surface outside the light extraction surface 10.

TABLE 2

| | | Illuminance (relative value) |
|---|---|---|
| Reference Example 1 | Electrode surface has mirror surface | 1.00 |
| Example 2 | Electrode surface has roughened surface | 1.07 |

The results of Table 1 and Table 2 confirm that the light diffusion surfaces (11b, 12b) formed on the surface of the electrode blocks (11, 12), the surface facing the light extraction surface 10, improves the light extraction efficiency.

Second Embodiment

A second embodiment of an ultraviolet irradiation device will be described, focusing mainly on the points where it differs from the first embodiment. The ultraviolet irradiation device 1 of the present embodiment differs from that of the first embodiment only in the location of the light diffusion surface.

Figure 12:
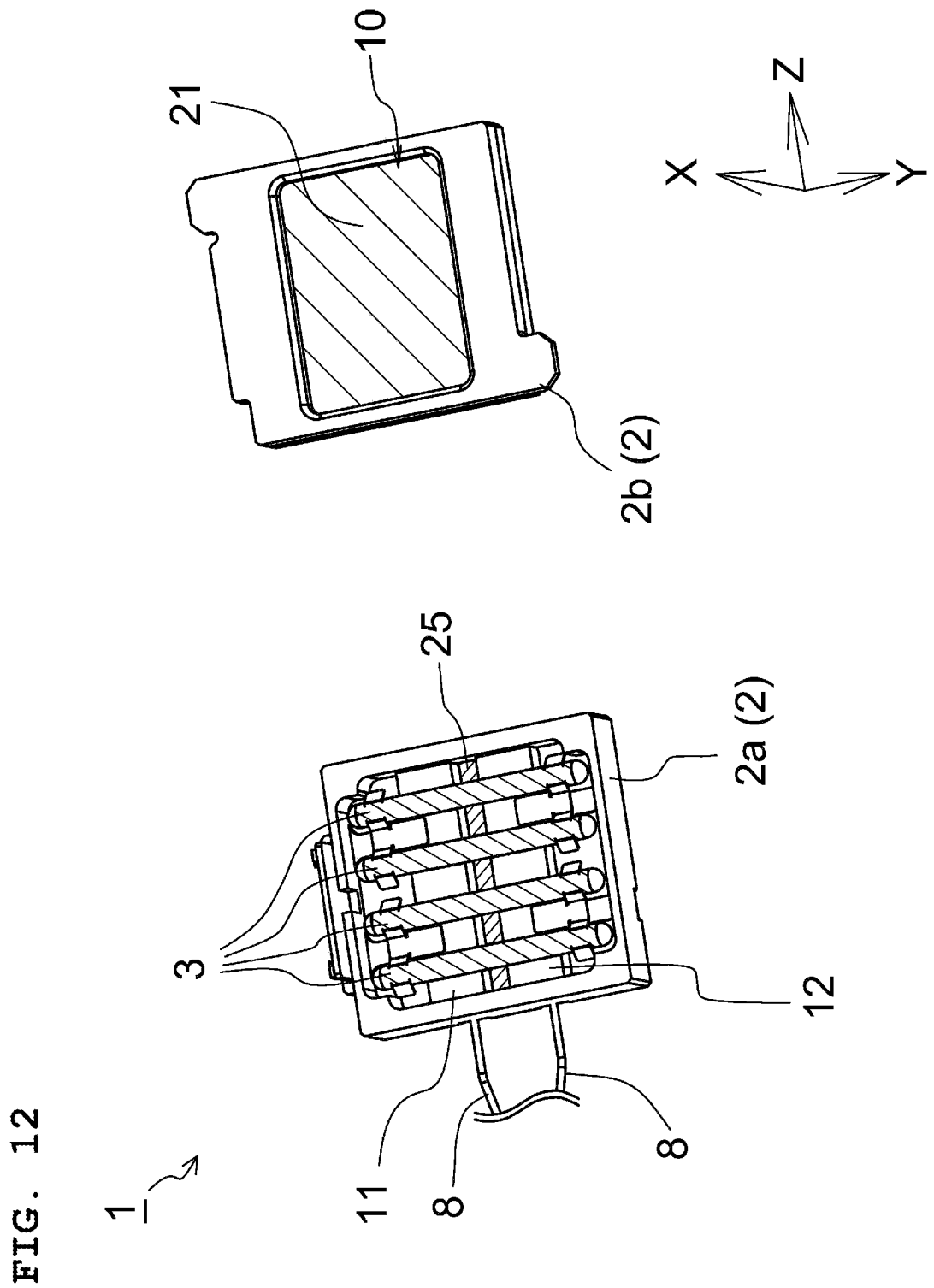
FIG. 12 is an exploded perspective view schematically illustrating an ultraviolet irradiation device of a second embodiment.
Figure 13:
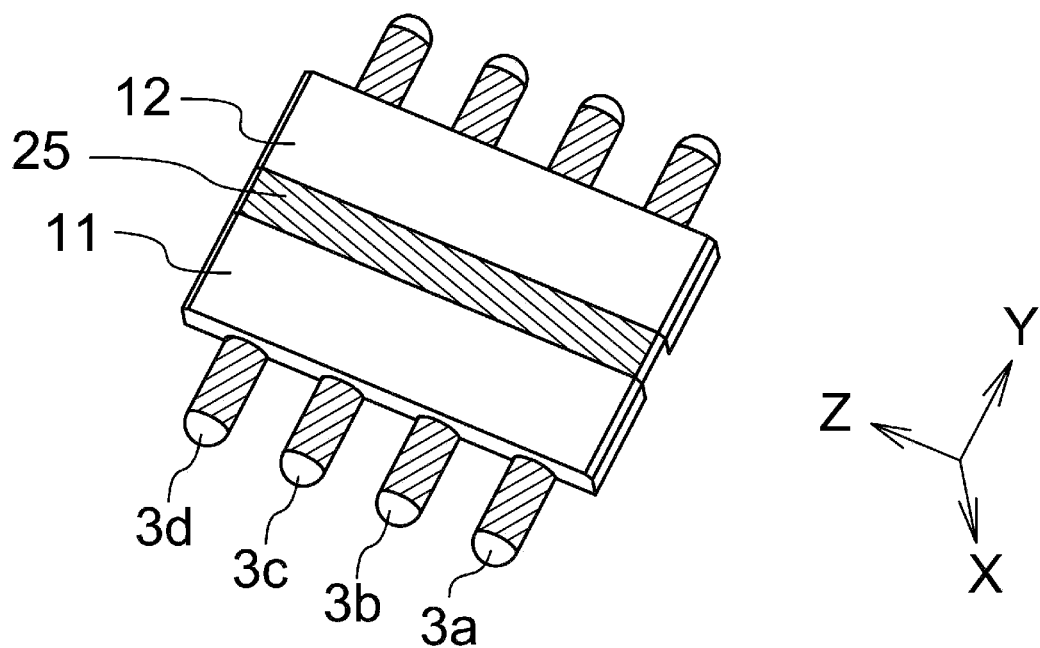
FIG. 13 is a perspective view schematically illustrating a structure of electrode blocks and excimer lamps provided in the ultraviolet irradiation device shown in FIG. 12.
Figure 14:
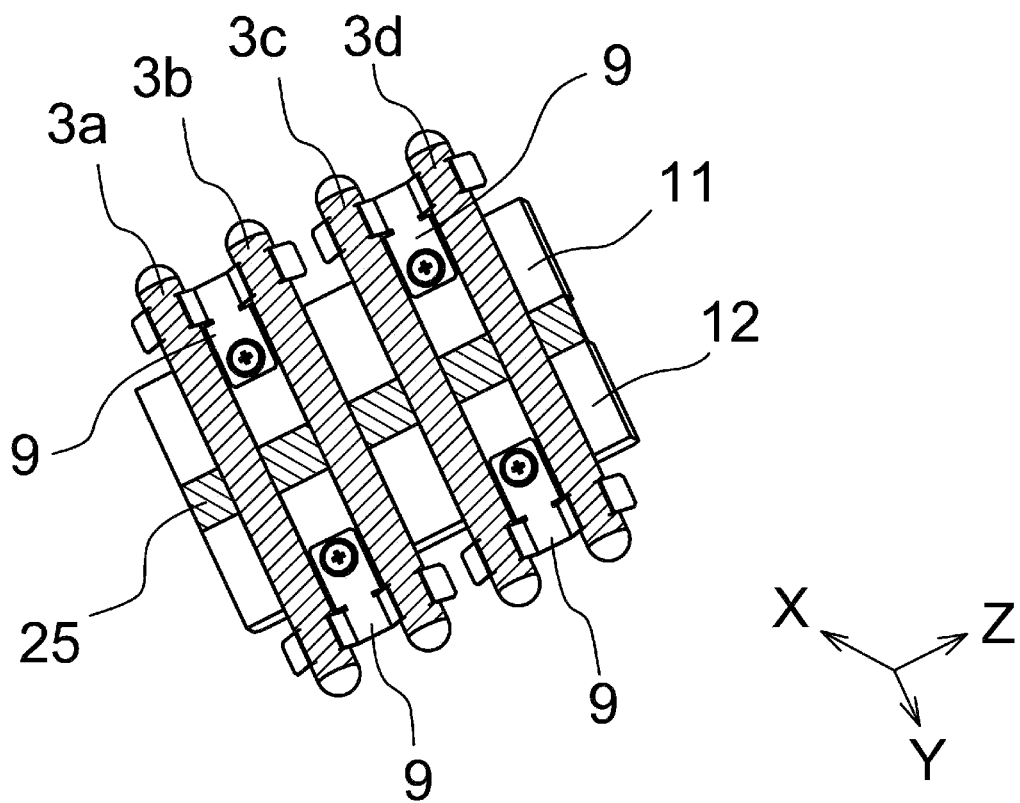
FIG. 14 is a perspective view with a viewing point different from that of FIG. 13.
Figure 15:
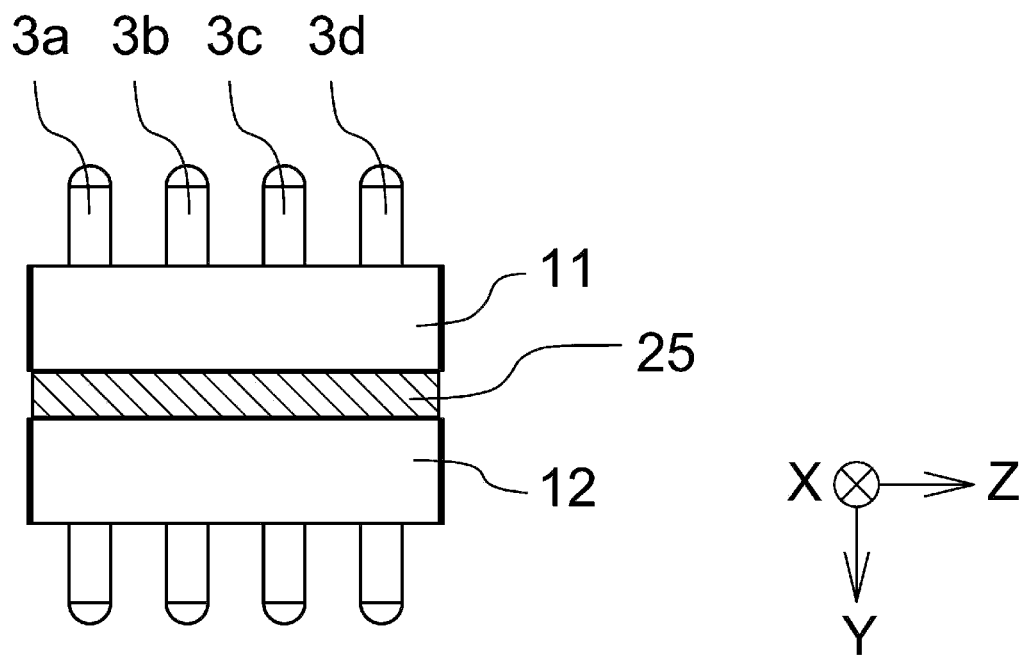
FIG. 15 is a schematic plan view of the excimer lamps in FIG. 13 as seen in the +X direction.

FIG. 12 is an exploded perspective view schematically illustrating the ultraviolet irradiation device of the present embodiment in a similar manner of FIG. 3. FIGS. 13 and 14 are perspective views omitting to illustrate the main body casing 2a, which constitutes the part of the lamp house 2, from FIG. 12, extracting only the electrode blocks (11, 12) and the excimer lamps 3 (3a, 3b, 3c, 3d) and illustrating them. FIGS. 13 and 14 are illustrated in a similar manner of FIGS. 4 and 5, respectively. FIG. 15 corresponds to a schematic plan view of the excimer lamps 3 in FIG. 13 as seen in the +X direction.

As shown in FIGS. 12 to 15, the ultraviolet irradiation device 1 of the present embodiment is provided with a light diffusion plate 25 between the electrode block 11 and the electrode block 12. This light diffusion plate 25 corresponds to a "first light diffusion plate". The light diffusion plate 25 can be, for example, a sheet material or a coated film consisting of fine particles of inorganic materials such as alumina and silica, or fine particles of fluorinated resin materials such as polytetrafluoroethylene (PTFE) formed on a surface of a glass member.

Figure 16:
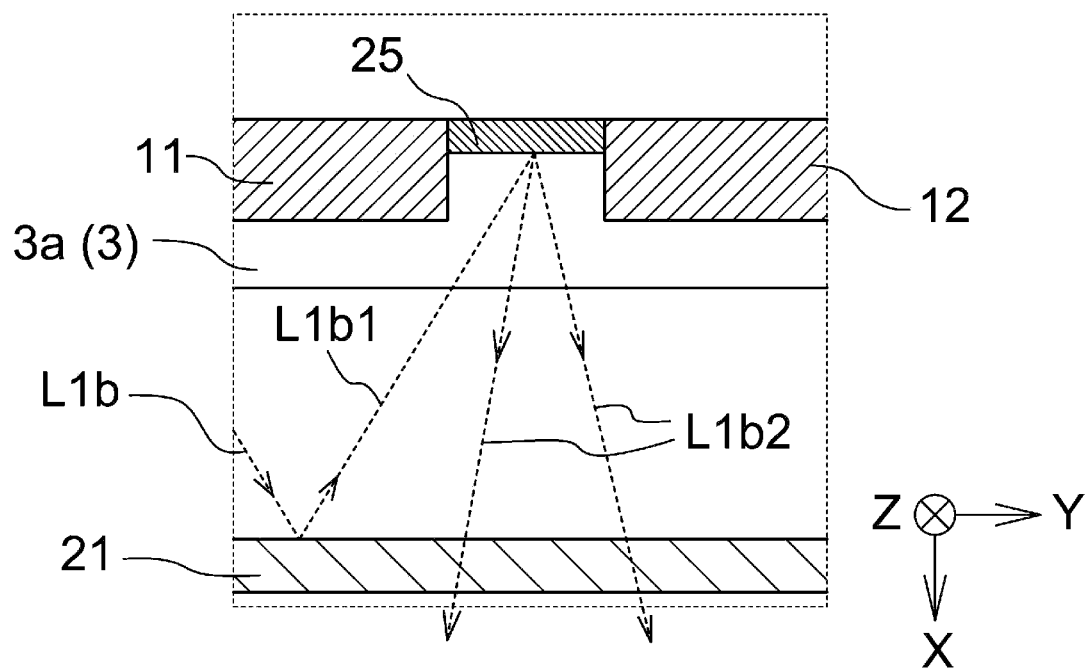
FIG. 16 is a partially enlarged view schematically illustrating the function of a light diffusion plate.

FIG. 16 is a partially enlarged view schematically illustrating the function of the light diffusion plate 25. As described above in the first embodiment, the ultraviolet light L1b, which has a relatively large incident angle with respect to the optical filter 21, is partially reflected by the optical filter 21 and travels toward the opposite side (−X direction) of the light extraction direction, that is, toward the electrode block (11, 12) (ultraviolet L1b1).

In the present embodiment, the light diffusion plate 25 is provided between the electrode block 11 and the electrode block 12. Hence, a part of the ultraviolet light L1b1 is incident on this light diffusion plate 25, thus diffused and reflected (ultraviolet light L1b2). A part of the ultraviolet light L1b2, which has been diffused and reflected, is incident on the optical filter 21 at an incident angle smaller than that of the ultraviolet light L1b. As a result, a part of the ultraviolet light L1b2 is transmitted through the optical filter 21 and is extracted outside the ultraviolet irradiation device 1. Therefore, this configuration improves light extraction efficiency compared to the case in which no light diffusion plate 25 is provided.

In the present embodiment of the ultraviolet irradiation device 1, as similar to the first embodiment thereof, the electrode blocks (11, 12) may also have their surfaces provided with the light diffusion surfaces (11b, 12b).

Third Embodiment

A third embodiment of an ultraviolet irradiation device will be described, focusing mainly on the points where it differs from the first embodiment. The ultraviolet irradiation device 1 of the present embodiment differs from that of the first embodiment only in the location of the light diffusion surface.

Figure 17A:
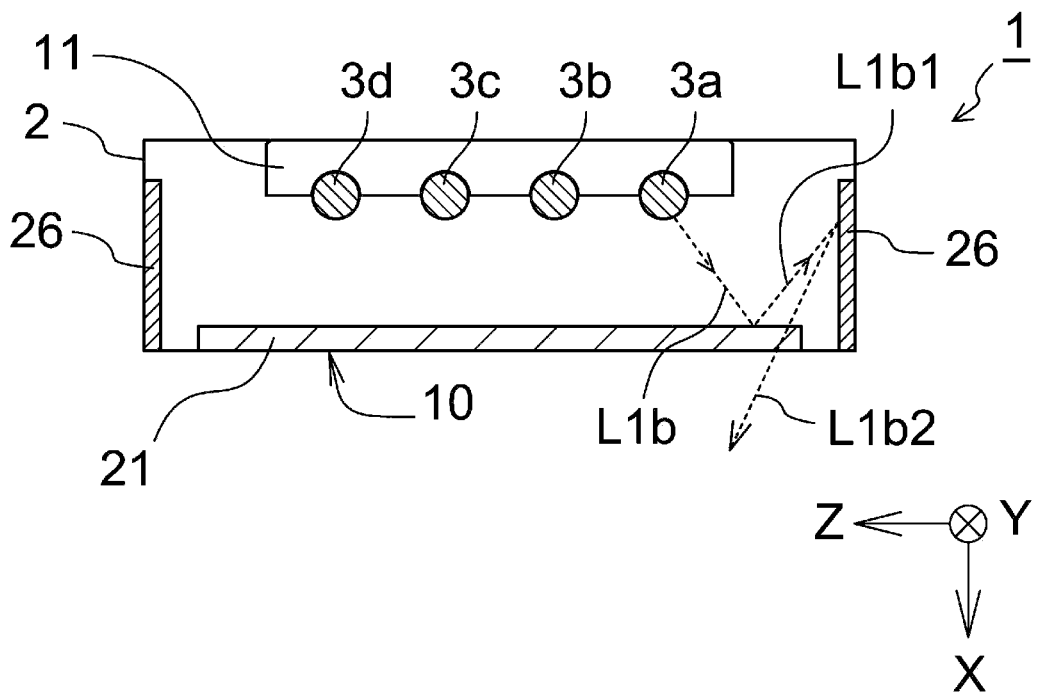
FIG. 17A is a cross-sectional view schematically illustrating an ultraviolet irradiation device of a third embodiment cut in a plain parallel to the XZ plain.
Figure 17B:
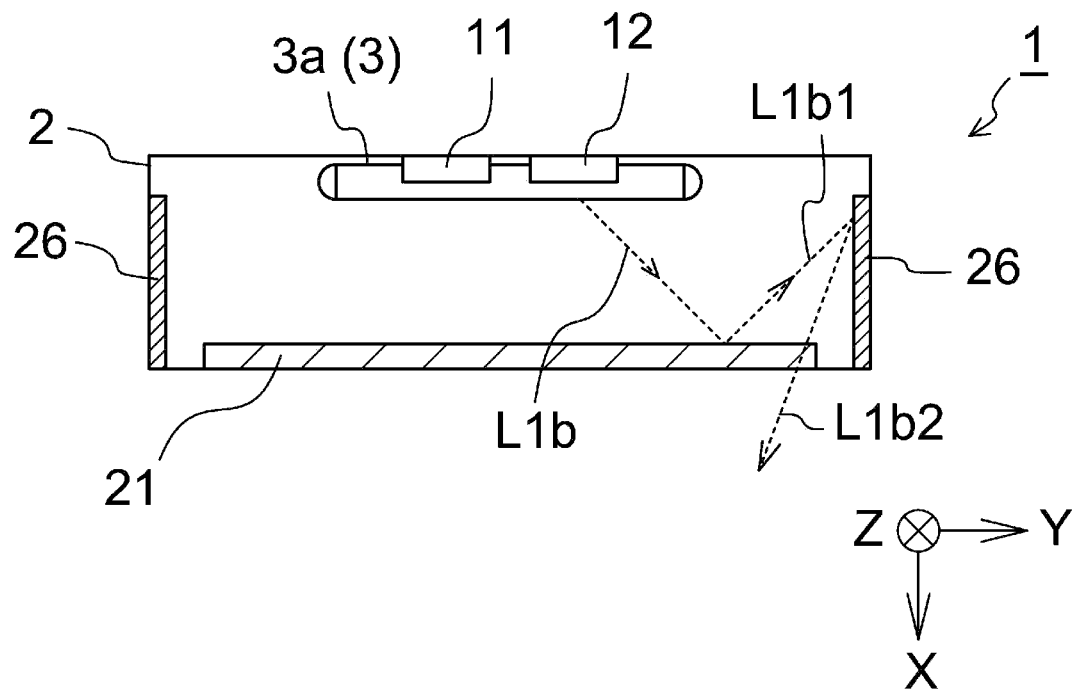
FIG. 17B is a cross-sectional view schematically illustrating the ultraviolet irradiation device of the third embodiment cut in a plain parallel to the XY plain.

FIGS. 17A and 17B are each a cross-sectional view schematically illustrating an ultraviolet irradiation device 1 of the present embodiment cut in a plain parallel to the XZ plain. FIG. 17A, as similar to FIG. 11, is a cross-sectional view schematically illustrating an ultraviolet irradiation device 1 cut in a plain parallel to the XZ plain at a predetermined position in the Y coordinate. FIG. 17B is a cross-sectional view schematically illustrating the ultraviolet irradiation device 1 cut in a plain parallel to the XY plain at a predetermined position in the Z coordinate.

As shown in FIGS. 17A and 17B, the ultraviolet irradiation device 1 of the present embodiment is provided with light diffusion plates 26 on an inner side surface of the lamp house 2. This light diffusion plate 26 corresponds to a "second light diffusion plate". The light diffusion plate 26 can be, as similar to the light diffusion plate 25 described above, a sheet material or a coated film consisting of fine particles of inorganic materials such as alumina and silica, or fine particles of fluorinated resin materials such as polytetrafluoroethylene (PTFE) formed on a surface of a glass member.

In the present embodiment, the light diffusion plates 26 are disposed along the inner side surface of the lamp house 2 to surround the optical filter 21 when viewed in the X direction.

As described above in the first embodiment, the ultraviolet light L1b, which has a relatively large incident angle with respect to the optical filter 21, is partially reflected by the optical filter 21 and travels toward the opposite direction (−X direction) of the light extraction direction. (ultraviolet light L1b1) In the present embodiment, since the light diffusion plates 26 are disposed on the inner side surface of the lamp house 2, a part of the ultraviolet light L1b1 is incident on the light diffusion plates 26, thus diffused and reflected (ultraviolet light L1b2). A part of the ultraviolet light L1b2, which has been diffused and reflected, is incident on the optical filter 21 at an incident angle smaller than that of ultraviolet light L1b. As a result, a part of the ultraviolet light L1b2 is transmitted through the optical filter 21 to the outside of the ultraviolet irradiation device 1. Therefore, this configuration improves light extraction efficiency compared to the case in which no light diffusion plate 26 is provided.

In the above embodiment, the light diffusion plates 26 are disposed to surround the optical filter 21 when viewed in the X direction. However, the light diffusion plates 26 are not necessarily disposed to surround the optical filter 21. For example, the light diffusion plates 26 may be disposed, when viewed in the X direction, to sandwich the optical filter 21 in the Y direction, or to sandwich the optical filter 21 in the Z direction.

Figure 18:
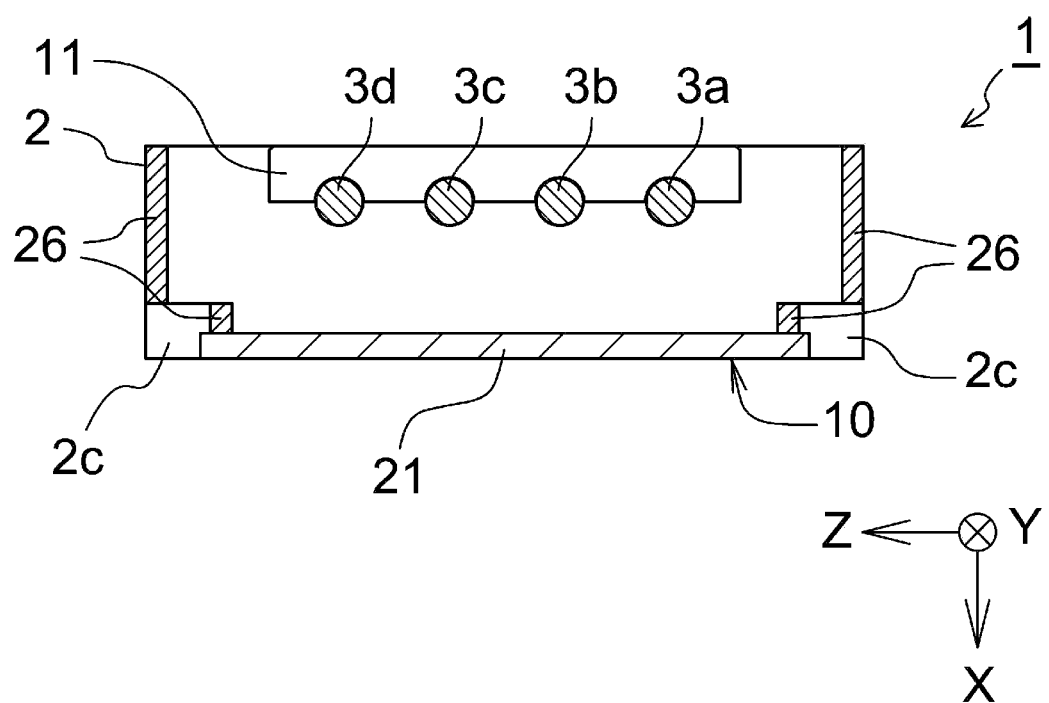
FIG. 18 is another cross-sectional view schematically illustrating the ultraviolet irradiation device of the third embodiment cut in a plain parallel to the XZ plain.

Incidentally, as shown in FIG. 18, the lamp house 2 can be provided with a mounting section 2c that is formed with a convex area protruding in the X direction to mount the light extraction surface 10 including the optical filter 21 in the lamp house 2. In this case, the inner side surface of the mounting section 2c can also be provided with the light diffusion plate 26. This configuration is able to shorten a separation distance between the excimer lamp 3 and the light diffusion plate 26 in the YZ plane, enabling the ultraviolet light L1b1 reflected by the optical filter 21 to be incident on the light diffusion plate 26 at a higher proportion. Note that, in FIG. 18, no light diffusion plate 26 may be provided on the inner side surface of the lamp house 2, and the light diffusion plate 26 may be provided only on the inner side surface of the mounting section 2c.

In the ultraviolet irradiation device 1 of the present embodiment, as similar to that of the first embodiment, the surface of the electrode blocks (11, 12) may be provided with the light diffusion surfaces (11b, 12b) thereon, and as similar to that of the second embodiment, the light diffusion plate 25 may be provided between the electrode block 11 and the electrode block 12.

Other Embodiment

The ultraviolet irradiation device 1 according to the above embodiments is described as being provided with the electrode blocks (11, 12) on the surface of which the excimer lamps 3 (3a-3d) are mounted. However, in the ultraviolet irradiation device 1 of the second embodiment and the third embodiment, the electrodes are not necessarily of a block type. For example, a conductive member constituting an electrode may be attached to the outer surface of the excimer lamp 3.

REFERENCE SIGNS LIST

1 Ultraviolet irradiation device
2 Lamp house
2a Main body casing
2b Lid
2c Mounting section
3 Excimer lamp
3a, 3b, 3c, 3d Excimer lamp
3G Luminescent gas
8 Power feed line
9 Holder
10 Light extraction surface
11 Electrode block
11a Mounting area
11b Light diffusion surface
12 Electrode block
12a Mounting area
12b Light diffusion surface 21 Optical filter
21N Normal line
25 Light diffusion plate
26 Light diffusion plate

The invention claimed is:

1. An ultraviolet irradiation device comprising:
a lamp house having at least one surface formed with a light extraction surface;
an excimer lamp that is accommodated in the lamp house at a position apart from the light extraction surface in a first direction, the excimer lamp emitting ultraviolet light having a main emission wavelength belonging to a first wavelength band of 190 nm or more and 225 nm or less;
a pair of electrodes that applies a voltage to a light-emitting tube of the excimer lamp;
an optical filter that is disposed on the light extraction surface, and that substantially transmits the ultraviolet light having the first wavelength band and substantially fails to transmit ultraviolet light having a wavelength of 240 nm or more and 300 nm or less; and
at least one light diffusion plate in the lamp house, a substantial portion being in front of the excimer lamp and flanking the optical filter and reflecting light incident on the light diffusion plate.

2. The ultraviolet irradiation device according to claim 1, wherein the light diffusion plate includes a second one of the light diffusion plate that is disposed in the lamp house in a manner to sandwich or surround the optical filter when viewed in the first direction.

3. The ultraviolet irradiation device according to claim 1, wherein the light diffusion plate includes a second one of the light diffusion plate that is disposed in the lamp house in a manner to sandwich or surround the optical filter when viewed in the first direction.

4. The ultraviolet irradiation device according to claim 1, wherein a luminescent gas containing KrCl or KrBr is sealed in the excimer lamp.

5. An ultraviolet irradiation device comprising:
a lamp house having at least one surface formed with a light extraction surface;
at least an excimer lamp each having a light-emitting tube that is accommodated in the lamp house at a position apart from the light extraction surface in a first direction, the excimer lamp emitting ultraviolet light having a main emission wavelength belonging to a first wavelength band of 190 nm or more and 225 nm or less;
a pair of electrodes having a mounting area for applying a voltage to the light-emitting tube of the excimer lamp and a light diffusion surface;
an optical filter that is disposed on the light extraction surface, and that substantially transmits the ultraviolet light having the first wavelength band and substantially fails to transmit ultraviolet light having a wavelength of 240 nm or more and 300 nm or less; and
a light diffuser that is disposed on the light diffusion surface of the electrodes at least between adjacent two of the light-emitting tubes in the lamp house for diffusing and reflecting light incident on the light diffuser.

6. The ultraviolet irradiation device according to claim 5, wherein the pair of electrodes includes a pair of electrode blocks that is disposed apart in an axial direction of the light-emitting tube of the excimer lamp such that a portion of each of the electrode blocks is in contact with a tube wall of the light-emitting tube thereof, and the light diffuser is formed on the light diffusion surface of at least one of the electrode blocks, the light diffusion surface facing the optical filter.

7. The ultraviolet irradiation device according to claim 6, wherein the light diffuser includes an uneven area formed on the surface of the electrode block.

8. The ultraviolet irradiation device according to claim 5, wherein a luminescent gas containing KrCl or KrBr is sealed in the excimer lamp.

9. An ultraviolet irradiation device comprising:
a lamp house having at least one surface formed with a light extraction surface;
at least an excimer lamp each having a light-emitting tube that is accommodated in the lamp house at a position apart from the light extraction surface in a first direction, the excimer lamp emitting ultraviolet light having a main emission wavelength belonging to a first wavelength band of 190 nm or more and 225 nm or less;
a pair of electrodes having a mounting area for applying a voltage to the light-emitting tube of the excimer lamp;
an optical filter that is disposed on the light extraction surface, and that substantially transmits the ultraviolet light having the first wavelength band and substantially fails to transmit ultraviolet light having a wavelength of 240 nm or more and 300 nm or less; and
a light diffuser that is disposed between the electrodes for diffusing and reflecting light incident on the light diffuser.

10. The ultraviolet irradiation device according to claim 9, wherein the light diffuser includes a first light diffusion plate that is disposed in the lamp house, on the opposite side of the light extraction surface in the first direction, and between the pair of electrodes.

11. The ultraviolet irradiation device according to claim 9, wherein a luminescent gas containing KrCl or KrBr is sealed in the excimer lamp.

* * * * *